United States Patent [19]

Kaneshiro

[11] Patent Number: 4,711,656
[45] Date of Patent: Dec. 8, 1987

[54] ENHANCEMENT OF NITROGEN-FIXATION WITH RHIZOBIAL TAN VARIANTS

[75] Inventor: Tsuneo Kaneshiro, Peoria, Ill.

[73] Assignee: The United States of America as represented by the Secretary of Agriculture, Washington, D.C.

[21] Appl. No.: 891,939

[22] Filed: Aug. 1, 1986

[51] Int. Cl.$^4$ ............................................. C05F 11/08
[52] U.S. Cl. ......................................................... 71/7
[58] Field of Search .......................................... 71/6, 7

[56] References Cited

U.S. PATENT DOCUMENTS 4,136,486  1/1979  Franklin, Jr. et al. ..................... 71/7

OTHER PUBLICATIONS

J. Badenoch-Jones et al., "Mass Spectrometric Identification of Indole Compounds Produced by *Rhizobium* Strains," Biomed. Mass Spec. 9(10): 429–437 (1982).
T. L. Wang et al., "Growth Regulators, *Rhizobium* and Nodulation in Peas . . . " Planta 155: 345–349 (1982).
T. Kaneshiro et al., "Tryptophan Catabolism to Indolepyruvic and Indoleacetic Acids by *Rhizobium japonicum* L-259 Mutants," Current Microbiol. 8: 301–306 (1983).
T. Kaneshiro et al., "Stimulated Nodulation of Soybeans by *Rhizobium japonicum* Mutant (B-14075) That Catabolizes the Conversion of Tryptophan to Indol-3yl-acetic Acid," Plant Sci. 42: 141–146 (1985).

*Primary Examiner*—Ferris H. Lander
*Attorney, Agent, or Firm*—M. Howard Silverstein; David G. McConnell; Curtis P. Ribando

[57] ABSTRACT

Legumes inoculated with tryptophan catabolic variants (tan variants) of wild-type bradyrhizobia are characterized by an enhanced capacity to fix atmospheric nitrogen as compared to parent strains. Responses of the symbiotic system to the variants include an auxinic stimulation of root growth, an enhancement of nodulation, and an increase in the nitrogen-fixation activities of the nodulated root systems.

4 Claims, No Drawings

ENHANCEMENT OF NITROGEN-FIXATION WITH RHIZOBIAL TAN VARIANTS

BACKGROUND OF THE INVENTION

1. Field of the Invention

The fixation of atmospheric nitrogen associated with specific legumes is the result of a highly specific symbiotic relationship with rhizobial bacteria. These indigenous bacteria dwell in the soil and are responsible for the formation of nodules in the roots of leguminous plants as sites for the nitrogen fixation. Currently, these rhizobia are classified by growth rate in free-living cultures, with the fast-growing organisms being designated as Rhizobium and the slow-growing organisms as Bradyrhizobium. Many of the rhizobial strains are not only host-specific but also differ with respect to capacity for effective symbiosis. Those strains which are able to infect a plurality of host plants across species or genus lines are said to be "cross-nodulating." Commercial inocula generally consist of a mixture of rhizobial strains to insure the widest potential for effective symbiosis within the appropriate crop. This invention therefore relates to the commercial practice of inoculating soybeans and other legume seedlings with specific rhizobia in order to increase effective nodulation and growth of leguminous crops.

1. Description of the Prior Art

In the art of soybean cultivation, unspecified strains of B. japonicum have become recognized as standard inoculants for initiating nodulation and nitrogen fixation. One strain of B. japonicum of interest is L-259 (USDA strain 26). When cultivated on artificial media, this strain in characterized by colorless colonies. Kaneshiro et al. [Current Microbiol. 8: 301-306 (1983)] report the discovery of tan-colored (tan), variant colonies which were selected and isolated from the colorless parent strain L-259 after enrichment and growth on a glutamate-limited medium supplemented with tryptophan (trp). These spontaneous variants retained the parental strain capacity for asymbiotic acetylene-reducing activity on a glutamate-mannitol-gluconate (GMG) medium; thereby indicating nitrogen-fixing capability. The variants were also reported to catabolize exogenous trp to over-produce indoleacetic acid (IAA), a plant auxin associated with new root formations in legumes, and indolepyruvic acid (IPA), a catabolic precursor to IAA. Kaneshiro speculated the significance of these variant strains as being useful in an assay for identifying nodule symbionts, though no in situ studies were reported.

R. lequminosarum [Wang et al., Planta 155: 345-349 (1982), and R. trifolii [Badenoch-Jones et al., Biomed. Mass Spec. 9: 429-437 (1982)] have been found to produce IAA and other indolic compounds without affecting legume nodulations significantly. These organisms in free-living cultures are estimated to produce indolic compounds in the range of less than 1 mg. per liter.

SUMMARY OF THE INVENTION

I have now surprisingly discovered that when a legume is inoculated with a tan variant isolated from a nodulating, Bradyrhizobium strain, and cultured in an environment conducive to symbiosis, the capacity for fixation of atmospheric nitrogen is significantly improved over that obtained by nodulation with the parent strain of the variant. Responses of the symbiotic system to the variant include an auxinic stimulation of root growth, an enhancement of nodulation as typified by increases in the number of nodules and overall volume of nodules per plant, and an increase in nitrogenase activity. The results are unexpected from the standpoint that the role of IAA in nodulation and the predictability between the asymbiotic and the symbiotic systems are substantially unresolved.

In accordance with this discovery, it is an object of the invention to enhance the potential in soybeans and other leguminous plants for symbiotic fixation of atmospheric nitrogen.

More particularly, it is an object of the invention to employ improved bradyrhizobia inocula in conjunction with leguminous crops.

These and other objects and advantages of the invention will become readily apparent from the ensuing detailed description.

DETAILED DESCRIPTION OF THE INVENTION

The method of this invention relies upon the use of trp catabolic variants of Bradyrhizobium bacteria. These variants are enriched and selected from wild-type strains grown on trp-supplemented media, such as by the procedure described in Kaneshiro et al., supra, herein incorporated by reference. When grown repeatedly in nitrogen-limited, agar medium containing L-trp, these subcultures produce colonies characterized by a tan pigmentation, facilitating selection from the wild-type and accounting for the nomenclature "tan variants" as used herein. It is anticipated that suitable tan variants can be isolated from the many symbiotic nitrogen-fixing bradyrhizobia. Of particular interest are those which are commonly employed for inoculating commercial legume varieties.

The tan variants of Bradyrhizobium bacteria selected in accordance with the above procedure are characterized by the ability to catabolize exogenously supplied trp to extracellular IAA and IPA. The IPA production is unique to the tan variants and is responsible for the orange-to-tan pigmentation observed when the organisms are grown on solid media. The orange color is an early manifestation of IPA production; whereas the tan-to-dark brown colors indicate later breakdown products of unstable IPA.

When cultured in GMG medium without trp, the variants produce colorless extracts devoid of significant IPA and IAA. The tan variants are typically characterized as having acetylene-reducing activity in free-living cultures that is approximately the same as parental strains. This activity, indicative of nitrogen-fixation capacity, can also be determined in the symbiotic system by acetylene reduction capacity of root nodules.

Specific tan variants which have been selected by this process have been derived from B. japonicum L-259 and have been identified as tan 4a, 4b, 20b, and 20d (NRRL accession nos. B-14074, B-14075, B-14076, and B-14077, respectively). These organisms have been reported by Kaneshiro et al., supra, and the procedure for their selection is described in Example 1, below.

Virtually all members of the legume family are candidate benefactors of the method of the invention. Without limitation thereto, plants which can be advantageously treated with an appropriate variant rhizobia include soybeans, cowpeas, lupines, and other legumes. Of principal interest are crop species, and particularly those which are routinely inoculated with specific rhizobial strains for the purpose of enhancing nodulation, nitrogen-fixation, or the general growth properties of the plant.

Inoculation of the leguminous plants with the tan variant strains may be conducted by conventional techniques as known in the art. Suitable inocula include culture broths and agronomically acceptable carrier medium containing cells of the organism. The inoculum may be applied to the seeds prior to planting or to the roots of seedlings after germination. Alternatively, the organism can be established in the locus of the plant, such as by incorporation into the soil before or after planting. In this regard, it would be advantageous to apply the inoculum in combination with other agronomic chemicals or adjuvants such as fertilizers and soil conditioners. The inoculum may comprise either a monoculture of a tan variant, a mixed culture of tan variants, or even a tan variant in combination with other rhizobia. It is also within the ambit of the invention to employ tan variants derived from rhizobial strains that can cross-nodulate between wild hosts and cultivated crops.

It is of course appreciated by the skilled artisan that dominance of competitive species is a factor in both infectivity and nodulation, and special precautions may therefore be necessary to insure infection of specific plants. Competition may arise from other indigenous organisms in the natural microflora of the soil. Compatibility of a particular rhizobial strain with soil and climatic conditions is another factor influencing symbiosis and requiring consideration as necessary.

Upon infecting the root tissue of the host plant, the tan variants initiate nodulation in essentially the same manner as the parental strains. The variants differ from the parental strains, however, in that they catabolize exogenous trp effectively, and produce much higher levels of auxinic indolics such as IAA and IPA extracellularly. For example, B. japonicum tan variants produce indolic compounds at a level of approximately 10 times (up to 40 mg. indolics per liter) that of the parent strain in free-living cultures. It is believed in light of this discovery that the increased levels of indolic compounds inside root nodules are responsible for stimulating enhanced nodulation and root growth in the host plant. These morphological responses are manifest by significant increases in the overall nodule volume and the fresh root weight. From a performance standpoint, legumes inoculated with the tan variants have superior nitrogen-fixation capacity as indicated by the acetylene reducing activity of the root system.

The following examples are intended only to further illustrate the invention and are not intended to limit the scope of the invention which is defined by the claims.

EXAMPLE 1

Isolation of tan variants.

*Bradyrhizobium japonicum* L-259 (USDA strain 26) was obtained from the Agricultural Research Service Culture Collection, Peoria, Ill. 61604. The organism was grown on a nitrogen-limited medium containing 0.3 g. L-glutamic acid (glu) and 0.5 g. L-tryptophan (trp) per liter. The complete medium contained glutamate-mannitol-gluconate (GMG) as nitrogen and carbon sources as set forth in Table I, below. Relative growth in liquid media was determined by turbidity with a "Klett-Summerson" colorimeter fitted with a 660 nm. filter ($Klett_{66}$). In the 0.3 g. glu medium, the wild-type strain L-259 gave a colorless but limited growth of 170 $Klett_{66}$ turbidity units. The aerobic, submerged culture incubated at 25° C. for 5 days on a rotary shaker (150 r.p.m.) was incubated further as a static culture for 15 days, yielding a tan broth. The broths were dark brown when 10% inocula were subtransferred twice more (14 days each incubation) into fresh N-limited medium containing 0.1 g. glu acid and 0.5 g. trp per liter. When limited by 0.1 g. glu per liter, growth was 85 $Klett_{66}$ turbidity units and yielded $15 \times 10^8$ colony-forming units (CFU) per ml.

Dark brown subcultures were diluted with saline and transferred to GMG agar plates containing 0.3 g. trp per liter (GMGT) to give 30–300 CFU per plate when incubated for 10–15 days at 28° C. Tan colonies (strains 4a, 4b, 20b and 20d) were selected from replicated

TABLE I

Composition of Nitrogen-Limited Glutamate-Mannitol-Gluconate (GMG) Growth Medium[a]

| Nutrient | Level (g./L.) |
| --- | --- |
| L-glutamic acid[b] | 0.3 |
| D-mannitol | 3 |
| potassium D-gluconate | 10 |
| $KH_2PO_4$ | 6 |
| $MgSO_4.7H_2O$ | 0.2 |
| $CaCl_2.2H_2O$ | 0.08 |
| agar | 15 |
| (Fe—Mo) citrate solution[c], 20 ml. | — |

[a]Adjusted to pH 6.65.
[b]Neutralized with NaOH after weighing. L-glutamic acid as a nitrogen source in GMG medium usually added at a level of 1 g./L.
[c]33.5 mg. $FeC_6H_5O_7.5H_2O$ and 7 mg. $Na_2MoO_4.2H_2O$ per 20 ml. and adjusted to slightly acidic pH with citric acid.

colonies differentiated on GMG and GMGT agar plates. Tan colony types grew as colorless replicas on GMG and as tan-colored replicas with orange-brown halos on GMGT agar. In liquid fermentations on glu-limited (0.3 g. per liter) media supplemented with trp, the tan isolates yielded orange broths within 4 days at 25° C. and turned dark orange-brown when incubated beyond 5 days. Maximal orange coloration ($Klett_{54}$ minus $Klett_{66}$ turbidity units=300) resulting from IPA elaboration was attained with approximately 0.5 g. trp per liter.

EXAMPLES 2–8

Product Analysis for Indolic Compounds.

Bradyrhizobium wild-type strains L-179 and L-344 from Indigofera hosts were screened for tan variants by the same procedures described in Example 1 for isolation of tan variants from *B. japonicum* L-259. To evaluate the potential in situ auxin producers and symbiotic nitrogen-fixers, these tan strains were assayed for asymbiotic indolic compound production in comparison to the parental strains and also in comparison to strain L-259 and its derived tan variants 4b and 20d.

The organisms were cultured in 5-day aerobic fermentations on a growth medium containing 37.5 mg. exogenous L-trp in 125 ml. broth. Fermented broths were centrifuged to remove cell particles, acidified with dilute HCl, and extracted with ethyl acetate (3 × 35 ml.). The pooled extract containing pigmented indolic compounds was vacuum evaporated to dryness. The residue was dissolved in 10 ml. ethyl acetate, washed with acidic water, and dried over anhydrous $Na_2SO_4$. The dried indolic extract was then dissolved in 0.5–2.0 ml. anhydrous ethyl acetate, and an aliquot (analytic range 1 to 8 μmoles per ml.) was esterified with diazomethane to quantify products by a GC/MS procedure. The resultant methyl esters were separated by GC in a methyl silicone fused silica capillary column. The separated GC peaks were analyzed by MS for characteristic fragment and molecular ions: IAA (m/z 130, 189), IPA (m/z 130, 217), and ILA (indole 3-lactic acid; m/z 130, 219). Indolic compounds were quantitated by MS in the single ion mode by comparison of areas with standard curves generated from reference compounds. The results are reported in Table II, below.

EXAMPLES 9-11

Root Nodulation Assay of Soybeans.

Tan variants 4b (NRRL B-14075) and 20d (NRRL B-14077) were evaluated against parental strains B. japonicum L-259 and B. japonicum USDA strain 110 for capacity to nodulate Glycine max L. (soybean) seedlings. The assay procedure of root nodulations in plastic growth pouches [Kaneshiro and Kwolek, Plant Sci. 42: 141-146 (1986)] was as follows:

Soybean Growth in Plastic Pouches.

Seeds of G. max L. cv Clark L-1 were surface-sterilized in ethanol for 2 min., treated with 1% (w/v) sodium hypochlorite for 10 min., and washed thoroughly with sterilized water. The soybeans were then suspended aseptically in water, aerated overnight at 27° C. with a sparger, and sterilized with hypochlorite a second time. By using this aseptic procedure, all 17 pouches from four sets of uninoculated soybeans were nodule-free. If uninoculated plants did not nodulate, examination of 2×2 contingency tables indicated that significant difference is attained with an exact probability above 95% using a minimum of four pouches/treatment. Accordingly, three swollen, germinating seeds were inoculated with either the parental strain or with the derived tan variant and planted in each plastic pouch (15×15 cm.) containing 25 ml. plant nutrients.

Seedlings were inoculated by soaking them for 2 h. in an inoculant mixture consisting of a large excess of cells ($10^6$ to $10^8$ CFU per ml.) from agar cultures washed into a plant nutrient

TABLE II

Extracellular Indolic Compounds Produced by Parental Rhizobia and Their Tryptophan (Trp) Catabolic Variants (Tan) When Grown in Medium Containing 184 μMoles L-Trp

| Example | Strain | Et acetate extract (mg.) | Indolic products (μmoles)[a] | | | % Conversion[b] |
|---|---|---|---|---|---|---|
| | | | IAA | ILA | IPA | |
| | Bradyrhizobium japonicum | | | | | |
| 2 | Partental L-259 | 1.9 | 1.70 | 0.00 | 0.00 | 1 |
| 3 | tan 4b | 25.2 | 5.80 | 0.60 | 5.80 | 7 |
| 4 | tan 20d | 23.6 | 10.90 | 1.70 | 6.10 | 10 |
| | Bradyrhizobium (Indiqofera host) | | | | | |
| 5 | Partental L-179 | 0.4 | 0.02 | 0.01 | 0.09 | 0 |
| 6 | tan 179 | 19.0 | 1.75 | 0.60 | 7.85 | 6 |
| 7 | Parental L-344 | 4.4 | 0.48 | 0.05 | 0.00 | 0 |
| 8 | tan 344 | 21.0 | 9.90 | 0.40 | 14.3 | 13 |

[a]μMoles product per fermentation flask.
[b]Total extracellular indolics produced from 184 μmoles trp (37.5 mg.) as determined by GC/MS.

mixture and, subsequently, covered with 0.2 ml. of the inoculum per pouched seedling. The 25-ml. plant nutrients were amended to contain 0.2 g. sucrose in the solution and 50 mg. insoluble $CaCO_3$ added into growth troughs per pouch. Each treatment or set of seedlings was replicated in 5-10 sterilized pouches and incubated aseptically under the folded flaps of the plastic pouches.

All soybean seedlings were cultivated on shelves illuminated by a mixture of warm-white fluorescent, incandescent filament, and natural lighting (16 h. light, 5-15 $Wm^{-2}$) at ambient temperatures until emergence of epicotyls (5-7 days).

The 7-day plants were thinned to one plant/pouch and the troughs of pouches were covered with sterile, nonabsorbent cotton. Plants were transferred to a growth chamber (16 h. light, 25° C.) irradiating 25 $Wm^{-2}$. Each pouch received three additions (5 ml., 3 ml., 3 ml.) of nitrogen-free plant nutrients at weekly intervals. Water that evaporated from growth pouches was replenished to the 20-40 ml. levels. Plants of the same set were harvested on the same day (20-30 days after inoculation) for comparisons. Under similar growth conditions, early nodulations in either plastic pouches or vermiculite-sand soils were detectable about 2 weeks after inoculation.

Analysis of Efficient Symbiosis.

Each plant was cut at the stem base, and the intact root system was weighed. Effective symbiotic nodulation/root was determined in two ways: (1) by estimated relative volume of all nodules ($kd.^3$ were k is $\pi/6$ and d is diameter in mm.); and (2) by AR specific activity (nmol. ethylene produced $h.^{-1}g.^{-1}$). Relative nodule volume/root was estimated by counting the sum of nodules and grading them into three groups: large nodule with approximately 4 mm. diameter (8 $kmm.^3$ volume), medium with 2 mm. (1 volume), and small with (1 mm. (0.13 volume). AR activity $h.^{-1}$ per g. fresh-root weight was measured by gas chromatography after the stemless roots with intact nodules were sealed in 25-ml. vials with an atmospheric mixture of 4 kPa acetylene and 100 kPa air. Root nodulations caused by strain L-259, when plants are grown in 26 plastic pouches using four different treatment parameters (Kaneshiro and Kwolek, supra), displayed significant correlation of AR activity with fresh-root weight (r=0.64) and estimated nodule-volume (r=0.74). Thus, effective symbioses are usually but not rigidly associated with good root formations when analyzed by root weight and nodule-volume.

Mean values, standard errors of the mean (S.E.=S/$\sqrt{n}$), and F-ratio tests were calculated. Analyses of variance (acceptable, comparative F-ratios where P<0.05) were used to establish significant treatment differences. Compared to parental strain L-259 (Example 9), tan variant 4b (Example 10) significantly increased symbiotic AR activity to approximately 1000 nmol. $h.^{-1}g.^{-1}$ when evaluated by F-ratio test (P<0.05). Seedlings infected with tan 4b also yielded better root growth (1.3 g. per plant; P<0.2) and nodule-volume (37 $kmm.^3$) than those infected with wild-type strain L-259. A highly effective strain USDA 110 (Example 11) gave intermediate results yielding 610 nmoles $h.^{-1}g.^{-1}$ AR activity and 21 $kmm.^3$ nodule-volume; but the mean root weight indicative of root growth was not significantly different from that infected with strain L-259. Compared to the collective root weights infected by strains USDA 110 and L-259, however, roots infected by tan 4b (Example 10) weighed significantly more (P<0.025). The results are reported in Table III, below.

EXAMPLES 12-14

Competitive Nodulation Between Tan and Wild-Type Strains.

Soybean (cv. Clark L-1) nodulations by combinations of inoculants

TABLE III

Comparative Nodulations of Soybean Seedlings cv. Clark L-1 Associated with
B. japonicum L-259 (USDA 26), Tan 4b, and B. japonicum Strain USDA 110

| Example | Strain | No. of plants | Fresh root wt. (g.)$^a$ | Estimated nodule-vol. (kmm.$^3$)$^a$ | Acetylene reducing activity (nmol. h.$^{-1}$g.$^{-1}$ ± S.E.)$^a$ |
|---|---|---|---|---|---|
| 9 | L-259 | 4 | 0.81 | 12 | 480 ± 80 |
| 10 | Tan 4b | 5 | 1.27 | 37 | 1040 ± 180 |
| 11 | USDA 110 | 7 | 0.85 | 21 | 610 ± 90 |

$^a$Data are mean values for root systems from composite sets. Plants were harvested at approximately 3 weeks after seed inoculation.

consisting of tan 4b mixed with strains L-259 or 110 were evaluated by essentially the same procedure as described in Examples 9–11. Inoculations consisting of 0.2 ml. diluted cultures were dripped onto roots after the third day of seed germination. To measure competition of the successful strains in root nodulations, determination of the proportion of each strain in the mixture (CFU per seed) is necessary. CFU, which indicate the viable, infective rhizobial cells, were determined by diluting cultures in sterile water and spreading aliquots of diluted cultures over the commonly used yeast extract-mannitol-gluconate-soil extract agar medium. These spread-plates were read after 7–14 days incubation at 25° C.

In addition, specific nodulations by test strains were deduced from tan-colored growth obtained after surface sterilizing the medium-to-large sized nodules (4–5 per plant) in 1% sodium hydrochlorite, crushing the washed nodules onto GMGT agar medium, and incubating the plates for 4–7 days. Specific nodulations by the tan variants were identified by their tan-to-orange colored confluent growth around crushed nodules. The results are reported in Table IV, below.

Nodules examined after root inoculation with tan 4b (Example 12) were uniformly tan colored in the presence of exogenous trp. However, the procedure used herein for the delayed and diluted inoculations of seedlings (Table IV) affected apparent AR activity adversely. Nodules resulting from mixed infections (Examples 13–14) gave better AR activity than those from tan 4b infection alone (P<0.10); but mixed infections always yielded nodules containing a mixture of tan- and non-colored rhizobia. Thus, the data indicate that tan variants do not overwhelm the root nodulation capacity but stimulate both root growth and AR activity. In other words, root nodulation sites in plants appear to be limited. Even so, tan variants or their compatible mixture with colorless strains infect plants to stimulate overall root growth and increase AR activity significantly.

It is understood that the foregoing detailed description is given merely by way of illustration and that modifications and variations may be made therein without departing from the spirit and scope of the invention.

TABLE IV

Competitive Nodulation of Soybean Seedlings by Tan 4b Coinoculated with Wild-Type Strains

| Example | Inoculum strain | Inoculum CFU$^a$ | No. of Plants | Analyses$^b$ of Root Per Plant | | |
|---|---|---|---|---|---|---|
| | | | | No. of tan nodules | Fresh wt. (g.)$^b$ | Acetylene reducing activity (nmole h.$^{-1}$g.$^{-1}$ ± S.E.) |
| 12 | Tan 4b | 130 × 10$^2$ | 6 | 28/28 | 1.14 | 680 ± 120 |
| 13 | Tan 4b + L-259 | 7 × 10$^3$ 4 × 10$^3$ | 6 | 10/27 | 1.32 | 1130 ± 190 |
| 14$^a$ | Tan 4b + USDA 110 | 1 × 10$^2$ 8 × 10$^2$ | 12 | 13/50 | 1.05 | 830$^c$ ± 80 |

$^a$CFU = colony-forming units per seed planted in the trough of plastic growth pouch. CFU for tan 4b in Example 14 ranged from 10$^1$ to 10$^3$ for an average of 10$^2$ CFU of tan 4b per seed.
$^b$Data are mean values for root systems from composite sets.
$^c$Mean of six plants AR activity.

I claim:

1. A method of improving the capacity of a leguminous plant for fixation of atmospheric nitrogen in symbiosis with a Bradyrhizobium bacterium comprising inoculating the plant or the locus of the plant with a tan variant of the parental strain of said bacterium and culturing the plant in an environment conducive to symbiosis.

2. The method as described in claim 1 wherein said leguminous plant is a soybean.

3. The method as described in claim 1 wherein said bacterium is a *Bradyrhizobium japonicum*.

4. The method as described in claim 1 wherein said tan variant is derived from the bacterium *Bradyrhizobium japonicum* L-259, and has the identifying characteristics of a variant selected from the group consisting of NRRL B-14075 and NRRL B-14077.

* * * * *